(12) United States Patent
Yamakawa

(10) Patent No.: US 7,922,973 B2
(45) Date of Patent: *Apr. 12, 2011

(54) COMBINED UNIT OF HUMIDITY INDICATOR AND DESICCANT PACK

(75) Inventor: Yoichi Yamakawa, Tokyo (JP)

(73) Assignee: AP Tech Corp., Hyogo (JP)

( * ) Notice: Subject to any disclaimer, the term of this patent is extended or adjusted under 35 U.S.C. 154(b) by 452 days.

This patent is subject to a terminal disclaimer.

(21) Appl. No.: 11/919,881

(22) PCT Filed: May 24, 2007

(86) PCT No.: PCT/JP2007/061045
§ 371 (c)(1),
(2), (4) Date: Nov. 5, 2007

(87) PCT Pub. No.: WO2007/142105
PCT Pub. Date: Dec. 13, 2007

(65) Prior Publication Data
US 2009/0311140 A1     Dec. 17, 2009

(30) Foreign Application Priority Data

May 31, 2006  (JP) ................ 2006-177245

(51) Int. Cl.
*G01N 21/00*   (2006.01)
*G01N 31/22*   (2006.01)
*G01D 21/00*   (2006.01)
*B65D 85/00*   (2006.01)
*G01N 7/00*    (2006.01)

(52) U.S. Cl. ....... 422/58; 116/206; 206/459.1; 73/29.01

(58) Field of Classification Search .................... 422/58; 116/206
See application file for complete search history.

(56) References Cited

U.S. PATENT DOCUMENTS 5,875,892 A * 3/1999 Martin et al. ............. 206/459.1
6,324,896 B1 * 12/2001 Aoyagi et al. ............. 73/29.01
7,316,198 B2 * 1/2008 Yamakawa ................ 116/206

FOREIGN PATENT DOCUMENTS

JP   11-347339 A   12/1999
JP   2005-164563 A   6/2005
TW   421714 B   2/2001

OTHER PUBLICATIONS

"Polyethylene" online article, 2010, <www.wikipedia.com>.*

* cited by examiner

Primary Examiner — Sam P Siefke
Assistant Examiner — Bryan T Kilpatrick
(74) Attorney, Agent, or Firm — Arent Fox LLP

(57) ABSTRACT

A combined unit of a humidity indicator and a desiccant pack is provided in which the humidity indicator (I) has one end portion bonded to one end portion of the desiccant pack (D) and can pivot around between a standby position (Ia) in which the indicator (I) overlaps one face of the desiccant pack (D) and an in-use position (Ib) in which it overhangs outside from one end edge (De) of the desiccant pack (D)), with the pivot center in the bonding portion or the vicinity thereof. This enables the humidity indicator to overlap the desiccant pack in the standby position when it is in an unused state, and after being enclosed within a packaging bag the humidity indicator and the desiccant pack can be kept as far away from each other as possible within the packaging bag, thus enabling detection of the humidity of the interior of the bag to be carried out precisely and appropriately.

7 Claims, 10 Drawing Sheets

COMBINED UNIT OF HUMIDITY INDICATOR AND DESICCANT PACK

CROSS-REFERENCE TO RELATED APPLICATION

This application is a U.S. National stage of International Application No. PCT/JP2007/061045, filed May 24, 2007, which claims the priority of Japan Application No. 2006-177245, filed May 31, 2006, the entire specifications, claims and drawings of which are incorporated herewith by reference.

TECHNICAL FIELD

The present invention relates to a combined unit of a card-shaped humidity indicator and a desiccant pack.

BACKGROUND ART

As the above humidity indicator, there is a conventionally known structure in which a humidity determining plate, formed by impregnating a card-shaped base paper with a moisture-sensitive material that changes color due to absorption of moisture (e.g. cobalt chloride), has provided on the front face a determining face as a humidity determining section where the moisture-sensitive material is exposed, and determination of the humidity in the environment around the base paper is carried out visually by a change in color (in the case of cobalt chloride, blue to pink) of the moisture-sensitive material on the determining face.

Such a humidity indicator is used in the transport, etc. of various types of industrial products that dislike moisture (e.g. electronic components such as circuit boards in which cracks may be caused by an epoxy-based resin absorbing moisture) by being enclosed together with the product and a desiccant pack within a transparent gas-tight packaging bag. That is, when the product is transported in such a usage state, since whether or not the humidity within the packaging bag exceeds a specified limit can be determined visually from the color of the humidity determining face of the humidity indicator, it is possible to simply check whether or not the interior of the packaging bag containing the desiccant pack has been kept in appropriate humidity conditions (dry conditions), and because of this such a humidity indicator is conventionally used widely in the electronic industry, etc.

DISCLOSURE OF INVENTION

Problems to be Solved by the Invention

Conventionally, when the product is enclosed within the packaging bag, the desiccant pack and the humidity indicator are taken out of separate storage containers used exclusively therefor and placed together within the packaging bag, and in order to carry out detection of the humidity of the interior of the packaging bag precisely and appropriately it is desirable that in this process the desiccant pack and the humidity determining face of the humidity indicator are spaced by at least a fixed distance within the bag. Because of this, storage management of the desiccant pack and the humidity indicator and the operation of enclosing them within the packaging bag are relatively troublesome and, moreover, there is a possibility that the desiccant pack and the humidity indicator thus enclosed might move close to each other due to vibration, etc. within the bag and come into contact with each other.

Furthermore, in the conventional humidity indicator, since its humidity determining face is exposed to the outside, when it is taken out into the atmosphere from a storage container used exclusively therefor whose interior is kept in a low humidity state or the above-mentioned desiccant pack-containing packaging bag, the humidity determining face changes color relatively quickly by direct contact with air within a room, thus causing the following problems. That is, if, when the packaging bag is opened and the humidity indicator is taken out, its humidity determining face changes color in a relatively short time, a worker might fail to notice the color before the change and make an erroneous assessment and, moreover, if, when an unused humidity indicator is taken out of a storage container used exclusively therefor and transferred to the packaging bag, the color changes before transfer due to clumsy operation, etc., a user might erroneously consider the humidity indicator to be a defective product, thus causing various problems.

Moreover, conventionally, the base paper of the humidity indicator is formed from a paper such as a filter paper, but such a paper, particularly a filter paper, easily generates fine dust (paper fragments, fiber, etc.) from an outer face or a cut face thereof, and when it becomes attached to an electronic component the performance thereof might be affected, thus making it desirable that dust generated from the base paper does not diffuse to the exterior.

The present invention has been accomplished in the light of the above-mentioned circumstances, and it is an object thereof to solve the above-mentioned conventional problems by a simple structure.

Means for Solving the Problems

In order to attain the above object, according to a first aspect of the present invention, there is provided a combined unit of a humidity indicator and a desiccant pack, the combined unit comprising: a humidity indicator having at least one humidity determining section provided on a front face of a card-shaped humidity determining plate made of paper and enabling humidity determination to be carried out by a change in color of the humidity determining section accompanying the absorption of moisture; and a desiccant pack placed together with a moisture-disliking article within a packaging bag for housing the article, wherein the humidity indicator has one end portion bonded to one end portion of the desiccant pack, and the indicator can pivot around between a standby position in which the indicator overlaps one face of the desiccant pack and an in-use position in which the indicator overhangs outside from one end edge of the desiccant pack, with a pivot center in the bonding portion or the vicinity thereof.

According to a second aspect of the present invention, there is provided a combined unit of a humidity indicator and a desiccant pack, the combined unit comprising: a humidity indicator having at least one humidity determining section provided on a front face of a card-shaped humidity determining plate made of paper and enabling humidity determination to be carried out by a change in color of the humidity determining section accompanying the absorption of moisture; and a desiccant pack placed together with a moisture-disliking article within a packaging bag for housing the article, wherein the humidity indicator has one end portion bonded to one end portion of the desiccant pack, and the indicator can pivot around between a standby position in which at least the humidity determining section of the indicator overlaps one face of the desiccant pack and an in-use position in which at least the humidity determining section of the indicator overhangs outside from one end edge of the desiccant pack, with a pivot center in the bonding portion or the vicinity thereof.

According to a third aspect of the present invention, in addition to the first or second aspect, the front face of the humidity determining plate made of paper is exposed to the outside, and an outer face of one end portion of the humidity determining plate separate from the humidity determining section is bonded to an outer face of one end portion of the desiccant pack.

According to a fourth aspect of the present invention, in addition to the first aspect, the humidity indicator has a transparent first resin film covering the front face of the humidity determining plate made of paper and a second resin film covering a back face of the determining plate, and peripheral edge portions of the two films are bonded to each other along their entire peripheries at a position jutting out from the outer peripheral edge of the humidity determining plate, a flat air layer is formed between the first resin film and the front face of the humidity determining plate, the entire area of the humidity determining section facing the air layer, a plurality of small holes providing direct communication between the air layer and the atmosphere are formed in the first resin film while being spaced from each other, and an outer face of one end portion of either one of the resin films is bonded to an outer face of one end portion of the desiccant pack.

According to a fifth aspect of the present invention, there is provided a combined unit of a humidity indicator and a desiccant pack, the combined unit comprising: a humidity indicator having at least one humidity determining section provided on a front face of a card-shaped humidity determining plate made of paper and enabling humidity determination to be carried out by a change in color of the humidity determining section accompanying the absorption of moisture; and a desiccant pack placed together with a moisture-disliking article within a packaging bag for housing the article, wherein the humidity indicator has a transparent first resin film covering the front face of the humidity determining plate and a second resin film covering a back face of the determining plate, and peripheral edge portions of the two films are bonded to each other by thermal bonding along their entire peripheries at a position jutting out from the outer peripheral edge of the humidity determining plate, a flat air layer is formed between the first resin film and the front face of the humidity determining plate, the entire area of the humidity determining section facing the air layer, and a plurality of small holes providing direct communication between the air layer and the atmosphere are formed in the first resin film while being spaced from each other, one end edge portion of one of the resin films extends further outside than corresponding one end edge portion of the other resin film, an extended portion thereof is bonded by thermal bonding to one end portion of the desiccant pack, and the humidity indicator can pivot around between a standby position in which the indicator overlaps one face of the desiccant pack and an in-use position in which the indicator overhangs outside from one end edge of the desiccant pack, with the pivot center in the thermal bonding portion or the vicinity thereof.

According to a sixth aspect of the present invention, in addition to any one of the first, second, fourth and fifth aspects, the humidity determining section faces the outside when the humidity indicator is in the standby position.

According to a seventh aspect of the present invention, in addition to the fourth or fifth aspect, at least the one of the resin films has a double layer structure of an outer resin layer and an inner resin layer integrally joined to an inner face of the outer resin layer, and the inner resin layer is a bonding layer having a lower melting point than that of the outer resin layer.

Effects of the Invention

As hereinbefore described, in accordance with the present invention, since the humidity indicator and the desiccant pack can be stored and managed within a storage container in a state in which the two are united as a combined unit, it is easy to carry out storage and management operations. Moreover, when the combined unit is in an unused state, the humidity indicator is made to overlap the desiccant pack in the standby position, and it is thus possible to minimize the space occupied within the storage container; furthermore, since the humidity indicator can be positioned in the vicinity of the desiccant pack until just before it is taken out of the storage container and placed within the packaging bag, it becomes possible to promptly and appropriately assess whether or not the indicator is a defective product by the color of the humidity determining section. When the combined unit is enclosed within the packaging bag, by pivoting the humidity indicator relative to the desiccant pack from the standby position to the in-use position, the humidity determining section of the humidity indicator and the desiccant pack can be kept as far away from each other as possible within the bag, and detection of the humidity of the interior of the bag can be carried precisely and appropriately and, moreover, since within a confined bag pivoting of the indicator back to the standby position can be prevented effectively, there is no possibility of the indicator moving unnecessarily close to the desiccant pack due to vibration, etc. during transport.

Furthermore, in accordance with the third aspect of the present invention in particular, it is unnecessary to cover the front and back of the humidity determining plate, which is made of paper, with a resin film, etc., and the cost can be reduced accordingly.

Moreover, in accordance with the fourth and fifth aspects of the present invention in particular, since the front and back of the humidity determining plate, which is made of paper, are covered by the first and second resin films respectively, and the outer peripheral edge portions of the two films are bonded by thermal bonding along the entire peripheries thereof at a position where they jut out from the outer peripheral edge of the humidity determining plate, even if fine dust is generated from the base paper of the humidity determining plate, it becomes difficult for dust to diffuse within the packaging bag due to the shielding by the resin films, and it is possible to prevent dust from affecting a product enclosed within the packaging bag. Furthermore, since the flat air layer is formed between the first resin film and the front face of the humidity determining plate, with the entire area of the humidity determining section facing the flat air layer, and the plurality of small holes providing direct communication between the air layer and the atmosphere are formed in the first resin film, when the humidity indicator is taken out of a storage container or a packaging bag, whose interior is kept in a low humidity state, into the atmosphere, it becomes possible to ensure that there is sufficient time until the color of the humidity determining section changes due to the humidity of the atmosphere, and this is effective in preventing the occurrence of erroneous assessment and problems when the time is too short. Furthermore, when a harmful material is contained in the humidity determining section, the two films can prevent the harmful material from coming into contact with one's body.

Moreover, in accordance with the fifth aspect of the present invention in particular, since one end edge portion of one of the resin films extends further outside than corresponding one end edge portion of the other resin film, the extended portion is bonded to one end portion of the desiccant pack by thermal bonding, and the humidity indicator can pivot around between a standby position in which the humidity indicator overlaps one face of the desiccant pack and an in-use position in which the humidity indicator overhangs outside from one end edge of the desiccant pack, with the pivot center in the thermal bonding portion or the vicinity thereof, the combined unit of the humidity indicator and the desiccant pack can easily be obtained by a simple thermal bonding structure that utilizes the thermal bonding properties of the resin films.

Furthermore, in accordance with the sixth aspect of the present invention in particular, since the humidity determining section faces the outside when the humidity indicator is in the standby position, it is possible to easily assess whether or not the indicator in the standby position is a defective product by the color of the humidity determining section exposed to the outside, and when making an assessment it is unnecessary to pivot the indicator.

Moreover, in accordance with the seventh aspect of the present invention in particular, since at least one of the resin films has the double layer structure of the outer resin layer and the inner resin layer integrally joined to the inner face of the outer resin layer, the inner resin layer being a bonding layer with a lower melting point than that of the outer resin layer, when carrying out the thermal bonding by means of a heat pressing machine that presses one of the resin films against the desiccant pack side while heating, by making the outer resin layer, with which the heat pressing machine is in direct contact, resistant to thermal melting (i.e. difficult for it to stick to the heat pressing machine), a thermal bonding operation between the one of the resin films and the desiccant pack can be carried out appropriately.

EXPLANATION OF REFERENCE NUMERALS AND SYMBOLS

Au Front side air layer
D Desiccant pack
DP Packaging bag
E Electronic component as article that dislikes moisture
F First resin film
F2 Second resin film
H Small hole
I Humidity indicator
Ia Standby position
Ib In-use position
M1 to M4 First to fourth humidity determining faces (humidity determining sections)
m, m', m" Thermal bonding (bonding)
P Humidity determining plate
U Combined unit
1 Outer resin layer
2 Inner resin layer

BEST MODE FOR CARRYING OUT THE INVENTION

Modes for carrying out the present invention are explained in detail below by reference to Embodiments of the present invention shown in the attached drawings.

Embodiment 1

Figure 1:
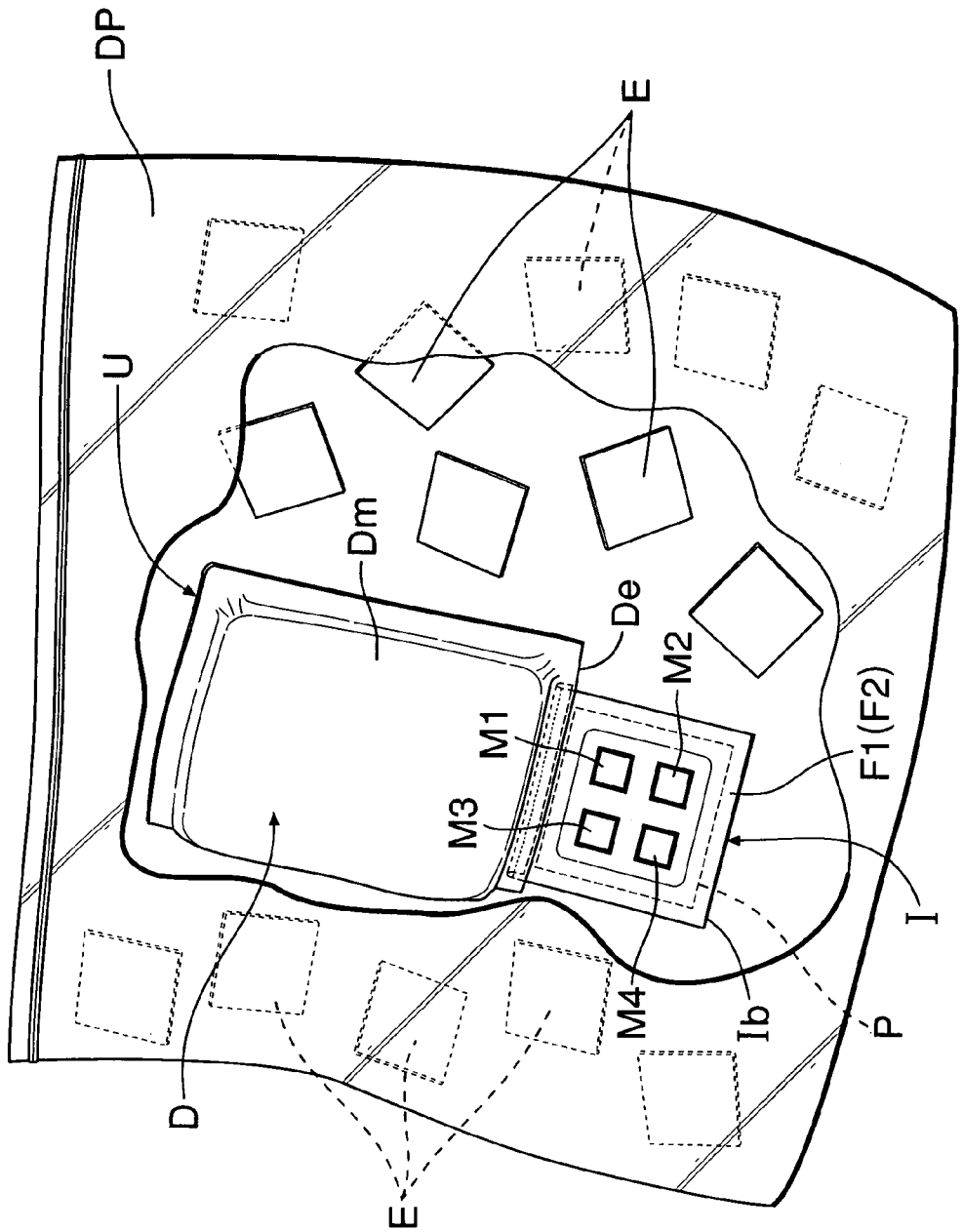
FIG. 1 is a partially cutaway overall view of a packaging bag for an electronic component showing a first embodiment of the present invention (Embodiment 1).
Figure 2:
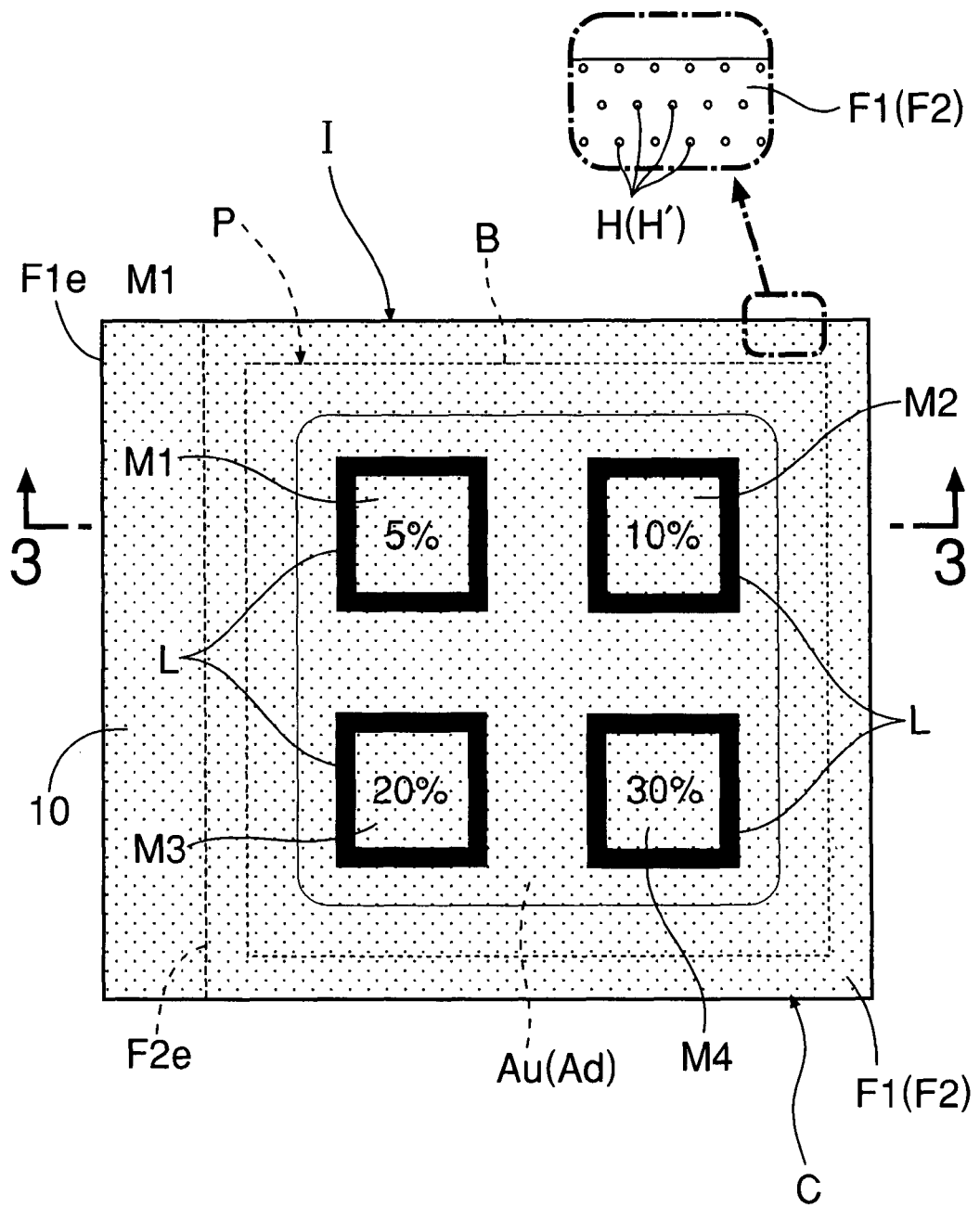
FIG. 2 is an element plan view showing a humidity indicator prior to being joined to a desiccant pack, and an enlarged partial view (Embodiment 1).

A first embodiment is now explained. In FIG. 1, a transparent gas-tight packaging bag DP is used for transporting an electronic component E such as a circuit board, which is an article that dislikes moisture, in a dry state. When the electronic component E is placed within the packaging bag DP, a desiccant pack D and a card-shaped humidity indicator I are enclosed together therewith, and the electronic component E is transported together with the packaging bag DP as a whole. During the transport thereof, since whether or not the humidity within the packaging bag DP has exceeded a specified limit can be determined visually by the color of humidity determining faces M1 to M4 of the humidity indicator I (whether or not the color has changed), it is possible to check simply whether or not the interior of the packaging bag DP containing the desiccant pack D has been kept in an appropriate dry state during transport.

The desiccant pack D is formed from a bag main body Dm and a desiccant (not illustrated) housed within the bag main body Dm, the bag main body Dm being formed in the form of a flat and rectangular bag from a synthetic resin or paper having air permeability and flexibility, and this desiccant pack D and the humidity indicator I are combined by a combining structure, which is descried later, thus forming a single combined unit U.

The structure of the combined unit U is now specifically explained by reference to FIG. 2 to FIG. 6.

First, the humidity indicator I is formed from a flat plate-form humidity determining plate P and a cover body C covering same. The humidity determining plate P includes a base paper B formed from a filter paper such as a hygroscopic filter paper, and cobalt chloride Co as a moisture-sensitive material retained on the base paper B; this base paper B is formed in the form of a card (a rectangle in the illustrated example) and has provided on its front face the humidity determining faces M1 to M4 as a plurality of humidity determining sections having cobalt chloride Co exposed thereon, and humidity determination is carried out by a change in color of the cobalt chloride Co on the humidity determining faces M1 to M4.

In the illustrated example, the first humidity determining face M1 has exposed thereon cobalt chloride Co that is adjusted in advance so that it remains blue when the humidity of the atmosphere in which the humidity indicator I is placed is 5% or less and changes to a pink color when the humidity increases beyond 5%, the second humidity determining face M2 has exposed thereon cobalt chloride Co that is adjusted in advance so that it remains blue when the humidity of the atmosphere is 10% or less and changes to a pink color when the humidity increases beyond 10%, the third humidity determining face M3 has exposed thereon cobalt chloride Co that is adjusted in advance so that it remains blue when the humidity of the atmosphere is 20% or less and it changes to a pink color when the humidity increases beyond 20%, and the fourth humidity determining face M4 has exposed thereon cobalt chloride Co that is adjusted in advance so that it remains blue when the humidity of the atmosphere is 30% or less and changes to a pink color when the humidity increases beyond 30%.

The plurality of humidity determining faces M1 to M4 are arranged two lengthwise and two widthwise in parallel in the illustrated example, but this arrangement may be freely chosen and, for example, they may be arranged all in line widthwise or lengthwise.

In the illustrated example, a cobalt chloride solution whose concentration is adjusted so as to exhibit color changing characteristics corresponding to each of the humidity determining faces M1 to M4 is dropped from above onto the base paper B and made to penetrate so that it is retained in the base paper B, and the front face of the base paper B corresponding to the position where the cobalt chloride solution has been dropped becomes the corresponding one of the humidity determining faces M1 to M4. A thick black line L is printed on the front face of the base paper B in an appropriate shape (a square in the illustrated example) so as to clearly display boundaries between the humidity determining faces M1 to M4 while neatly hiding the spread of the peripheral edge of the portion onto which the solution has been dropped and, moreover, a display (5%, 10%, 20%, 30%) of the humidity limit that can be checked by the humidity determining faces M1 to M4 is printed on each of the humidity determining faces M1 to M4 or the vicinity thereof. The structure of the humidity determining plate P explained above is conventionally known.

The cover body C is formed from a first resin film F1 covering the front face of the humidity determining plate P and a second resin film F2 covering the back face of the determining plate P. The first and second resin films F1 and F2 are formed in a rectangular shape so as to jut out from the outer peripheral edge of the humidity determining plate P along the entire periphery, and outer peripheral edges of the two resin films F1 and F2 are directly bonded to each other by thermal bonding m along the entire periphery, thus forming a flat rectangular bag.

Each of the resin films F1 and F2 is formed from a transparent synthetic resin film having thermal bonding properties, and in the illustrated example they have a double layer structure in which an outer resin layer 1 as a base layer formed from a tough synthetic resin material having a relatively high melting point and high strength (e.g. polyester, nylon, etc.) and an inner resin layer 2 as a bonding layer formed from a synthetic resin material having a relatively low melting point (e.g. polyethylene, EVA, etc.) are integrally joined to each other, and the thermal bonding m between the outer peripheral edges of the two films F1 and F2 is made by compression bonding the inner resin layers 2 and 2, which function as a bonding layer for each of the resin films F1 and F2, in a state in which they are in direct contact and are heated. In this case, since the relatively high melting point outer resin layer 1 of each of the resin films F1 and F2 is in direct pressure contact with a heat pressing machine such as a heat roll used for thermal bonding, the resin does not stick strongly to the heat pressing machine, and the processability is good.

Furthermore, the outer resin layer 1 is subjected to an antistatic treatment. With regard to a method for the antistatic treatment, for example, the outer resin layer 1 is kneaded with an antistatic agent, or the front face (face on the opposite side to the inner resin layer 2) of the outer resin layer 1 is subjected to antistatic processing. In accordance with such an antistatic treatment, the humidity determining plate P itself becomes resistant to electrostatic charging, the resin films F1 and F2 become resistant to dust becoming electrostatically attached thereto, and when the humidity indicator I is enclosed in the packaging bag DP together with the electronic component E it is therefore possible to minimize the influence of electrostatic charging or dust on the electronic component E.

Moreover, a flat front side air layer Au is formed between the first resin film F1 and the front face of the humidity determining plate P, the entire area of the plurality of humidity determining faces M1 to M4 facing the flat front side air layer Au. That is, the first resin film F1 is thermocompression bonded to the front face of the humidity determining plate P except in a region corresponding to the front side air layer Au, and a small gap generated between the first resin film F1 and the humidity determining plate P in the region that is not thermocompression bonded forms the front side air layer Au. In the illustrated example, the front side air layer Au is formed in the form of a flat plane encompassing all of the humidity determining faces M1 to M4 as a common air layer that all of the plurality of humidity determining faces M1 to M4 face.

Furthermore, a flat back side air layer Ad is formed between the second resin film F2 and the back face of the humidity determining plate P, at least a region of the back face corresponding to the humidity determining faces M1 to M4 (in the illustrated example, the entire area of the back face) facing the back side air layer Ad. This back side air layer Ad is formed in the same manner as for the front side air layer Au, which is described above.

The first resin film F1 has a large number of small holes H formed that are spaced from each other so as to provide direct communication between the front side air layer Au and the atmosphere, and the second resin film F2 also has a large number of small holes H' formed that are spaced from each other so as to provide direct communication between the back side air layer Ad and the atmosphere. In the illustrated example, for convenience of processing, the resin films F1 and F2 have small holes H and H' made over the entire area rather than only in areas corresponding to the air layers Au and Ad.

The inner diameter of the small holes H is set at a size such that, when a worker holds the humidity indicator I by hand, fingers that are in contact with each of the resin films F1 and F2 do not make direct contact with the cobalt chloride Co of the humidity determining faces M1 to M4 (in the illustrated example, the inner diameter is 0.8 mm). Moreover, the dispersion density and the inner diameter of the small holes H and H' are set so that, even when the humidity indicator I is taken out of a packaging bag in a low humidity state, a sealed container, etc. into the atmosphere, there is an appropriate time lag for the humidity of the air layers Au and Ad to change according to the humidity of the atmosphere, and it is therefore possible to prevent the cobalt chloride Co of the humidity determining faces M1 to M4 from changing color in a relatively short time, thus exhibiting an effect in preventing erroneous assessment and problems due to the color changing.

Figure 3:
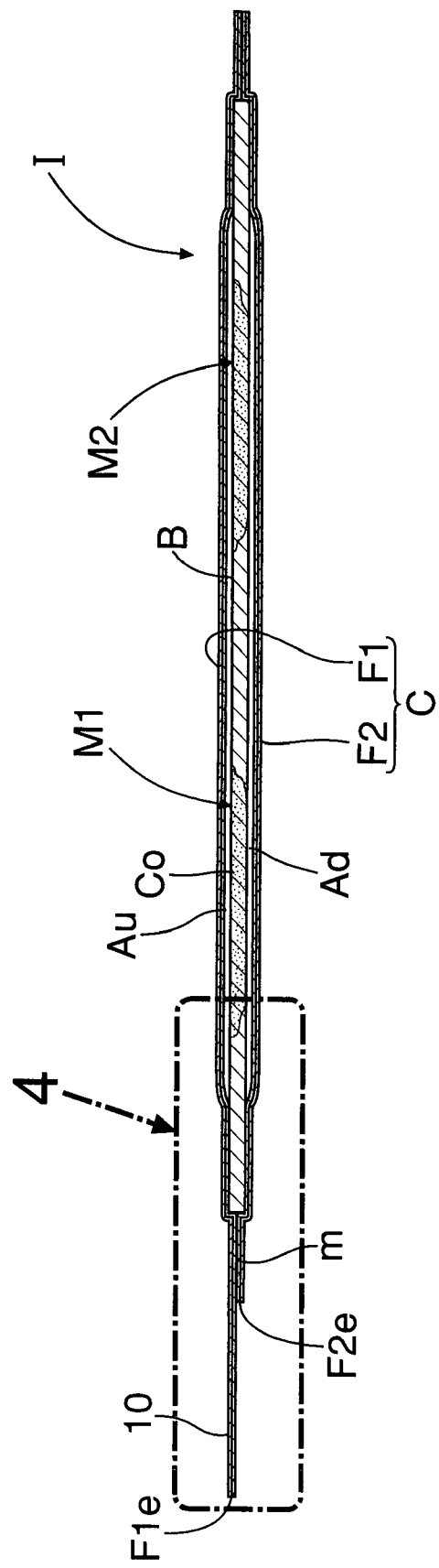
FIG. 3 is an enlarged vertical sectional view along line 3-3 in FIG. 2 (Embodiment 1).
Figure 4:
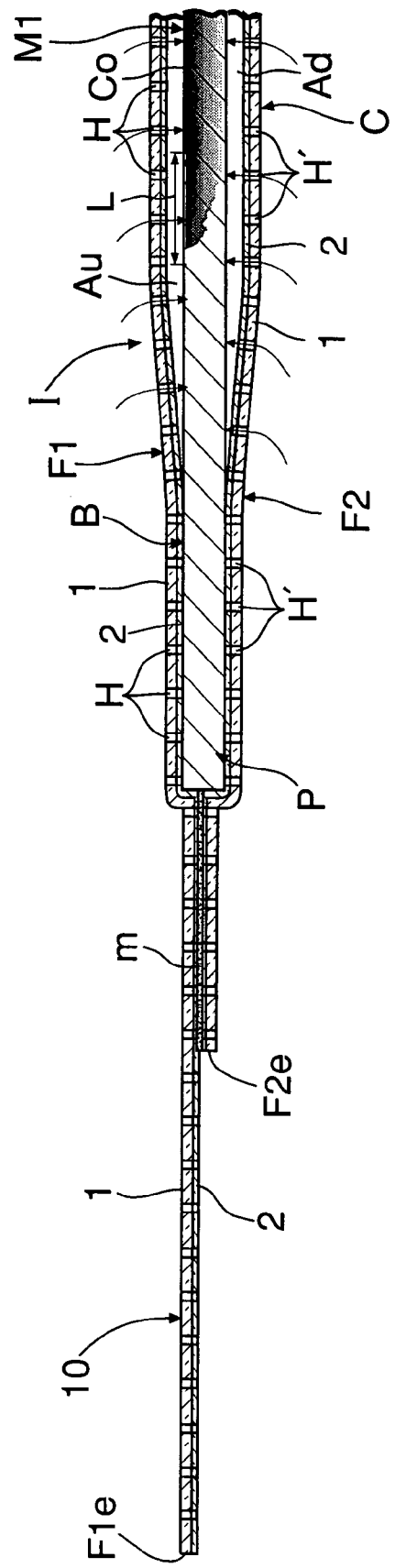
FIG. 4 is an enlarged sectional view of an arrowed part 4 in FIG. 3 (Embodiment 1).
Figure 5:
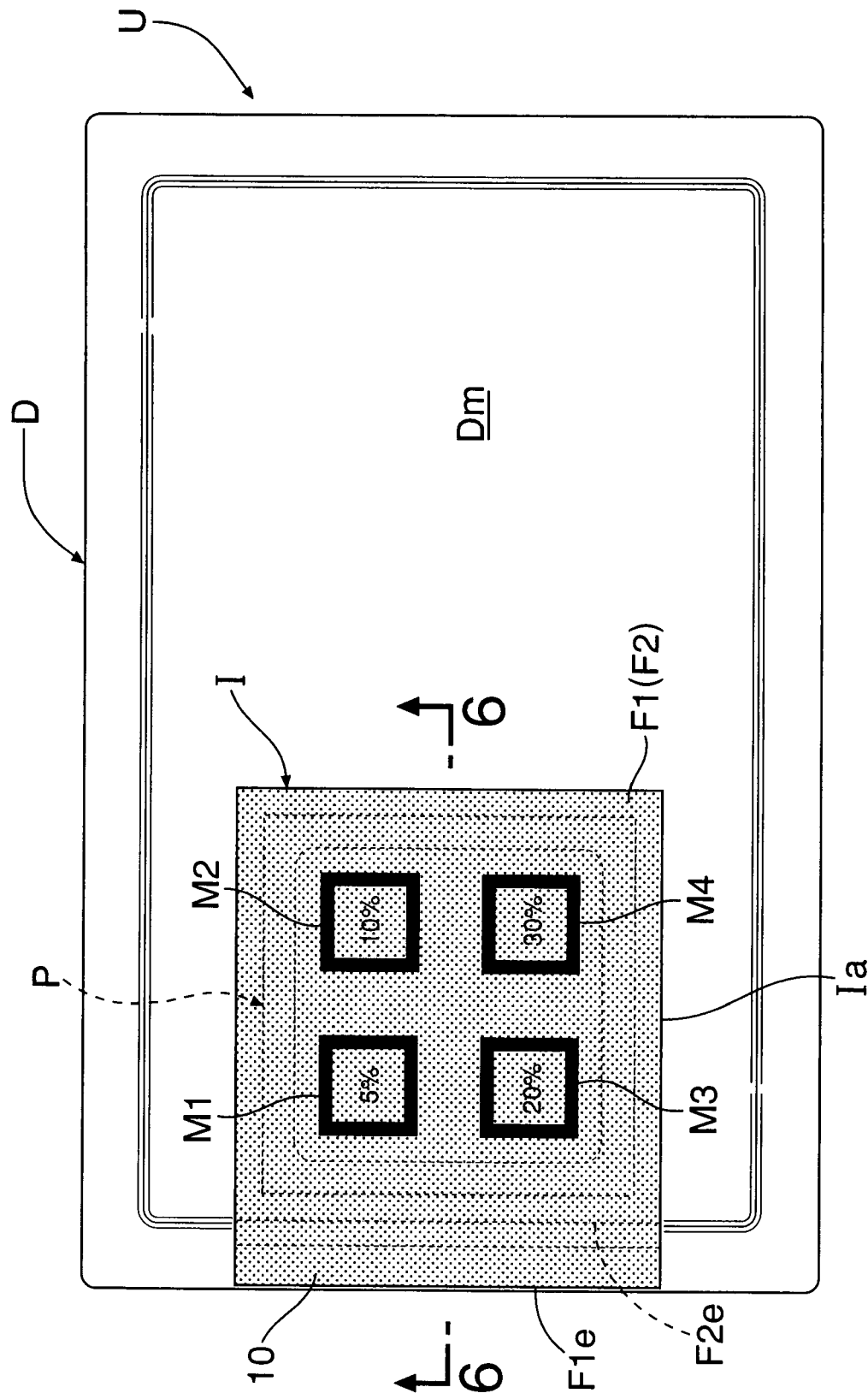
FIG. 5 is a plan view showing a combined unit of the humidity indicator and the desiccant pack (Embodiment 1).
Figure 6:
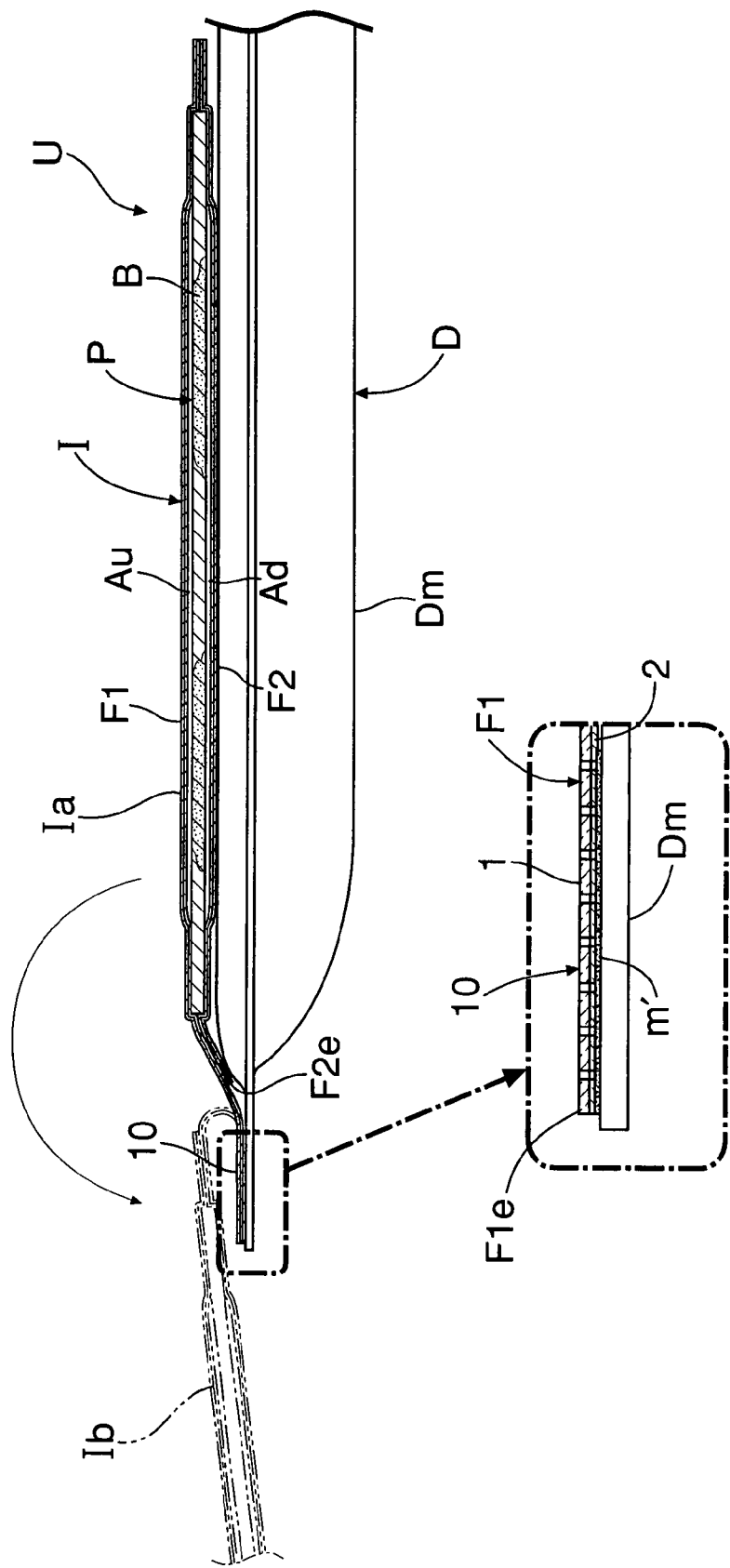
FIG. 6 is an enlarged sectional view along line 6-6 in FIG. 5 and an enlarged partial view thereof (Embodiment 1).

For example, in the present embodiment, 560 small holes H and H' having an inner diameter of 0.8 mm are pierced at equal intervals in each of the resin films F1 and F2, which are 40 mm square, and the dispersion density thereof is 35 holes/$cm^2$. In this case, the time taken for the cobalt chloride Co to completely change from blue to pink, although depending on the ambient atmospheric humidity, is approximately 5 to 7 min on the first humidity determining face (humidity limit 5%), approximately 15 to 20 min on the second humidity determining face (humidity limit 10%), approximately 30 to 35 min on the third humidity determining face (humidity limit 20%), and approximately 45 to 50 min on the fourth humidity determining face (humidity limit 30%). On the other hand, when the same humidity determining plate P is used in an exposed state without covering it with the cover body C, the time taken for the color to change is approximately 4 to 5 min on the first humidity determining face (humidity limit 5%), approximately 10 to 15 min on the second humidity determining face (humidity limit 10%), approximately 20 to 25 min on the third humidity determining face (humidity limit 20%), and approximately 35 to 40 min on the fourth humidity determining face (humidity limit 30%), and it can be understood that the time taken for the color to change is appropriately longer in the present embodiment. In FIG. 3, in order to make it easier to understand, the thickness of the air layers Au and Ad and of the resin films F1 and F2 is slightly exaggerated compared with the actual scale.

One end edge portion F1e of either one (in the illustrated example, the first resin film F1) of the first and second resin films F1 and F2 extends further outside than the corresponding one end edge portion F2e of the other resin film (in the illustrated example, the second resin film F2), an extended portion 10 thereof is bonded to one side end portion De, which is flexible, of the desiccant pack D by thermal bonding m', and the humidity indicator I can pivot between a standby position Ia in which the entirety thereof overlaps one face of the desiccant pack D and an in-use position Ib in which a majority thereof overhangs outside from one end edge of the desiccant pack D, with the pivot center in the thermal bonding portion m' or the vicinity thereof. The thermal bonding m' is carried out by placing the desiccant pack D on a processing stage (not illustrated), superimposing the inner resin layer 2 in the extended portion 10 of the film F1 on the one end edge portion of the one face of the desiccant pack D so as to be in contact therewith, and pressing from the outside of the extended portion 10 to the desiccant pack D side while heating by means of a heat pressing machine (not illustrated).

The operation of the first embodiment is now explained. The combined unit U of the humidity indicator I and the desiccant pack D of this embodiment is used by being enclosed within the transparent gas-tight packaging bag DP together with the electronic component E such as a circuit board as illustrated in FIG. 1 when transporting the moisture-disliking electronic component E, and the electronic component E is transported together with the packaging bag DP as a whole. During the transport, by visually assessing whether or not the humidity within the packaging bag DP exceeds a specified limit by the color of the humidity determining faces M1 to M4 of the humidity indicator I, it is possible to simply check whether or not the interior of the packaging bag DP containing the desiccant pack D is kept in an appropriate dry state during transport.

After the above-mentioned transport, when the packaging bag DP is opened and the electronic component E is taken out, a worker holds the combined unit U of the humidity indicator I and the desiccant pack D in their hand, takes it out of the bag, and checks the color of the humidity determining faces M1 to M4 of the indicator I, and since the front and back of the humidity determining plate P of the indicator I are covered by the first and second resin films F1 and F2, it is possible to prevent effectively the cobalt chloride Co, which is toxic, of the humidity determining faces M1 to M4 from becoming attached to the hand, and the worker can handle the indicator I with peace of mind. Furthermore, even if fine dust (paper cuttings, fiber, etc.) is generated from the base paper B of the humidity determining plate P, since the structure makes it difficult for the dust to diffuse outside due to shielding by the resin films F1 and F2, even when the indicator I is enclosed together with the dust-disliking electronic component E within the packaging bag DP, it is possible to prevent effectively dust from affecting the electronic component E.

The desiccant pack D and the humidity indicator I are joined to each other as described above and form the combined unit U, and as joining means a simple thermal bonding structure utilizing the thermal bonding properties of one of the first and second resin films (in the illustrated example, the first resin film F1) is employed, and this enables the combined unit U of the humidity indicator I and the desiccant pack D to be obtained with ease and low cost and makes its handling and storage management remarkably simple.

Furthermore, when the combined unit U is in an unused state, by making the humidity indicator I overlap the desiccant pack D in the standby position, the space occupied within a storage container can be minimized and, moreover, the humidity indicator I can be kept in a state in which it overlaps the desiccant pack D (that is, the closest state) until just before it is taken out of the storage container and placed into the packaging bag DP; it is therefore possible to promptly and appropriately assess whether or not the indicator I taken out of the storage container is a defective product from the color of the humidity determining faces M1 to M4. In this case, since the humidity determining faces M1 to M4 face the outside when the humidity indicator I is in the standby position Ia, it is possible to assess whether or not the indicator I in the standby position Ia is a defective product by the color of the externally exposed humidity determining faces M1 to M4.

Furthermore, when enclosing the humidity indicator I within the packaging bag DP, it is pivoted around from the standby position Ia to the in-use position Ib relative to the desiccant pack D. This enables the humidity indicator I and the desiccant pack D to be kept as far away from each other as possible within the packaging bag DP, and detection of the humidity of the interior of the bag can be carried out precisely and appropriately. Moreover, since the indicator I is prevented effectively from pivoting back to the standby position Ia within a confined bag, there is no possibility of the indicator I moving unnecessarily close to the desiccant pack D due to vibration, etc. during transport.

Furthermore, the flat front side air layer Au is formed between the first resin film F1 and the front face of the humidity determining plate P, the entire area of the first to fourth humidity determining faces M1 to M4 facing the air layer Au, and a large number of small holes H for providing direct communication between the air layer Au and the atmosphere are formed in the first resin film F1 while being spaced from each other. Because of this, when the humidity indicator I is taken out of the packaging bag DP, etc., which is kept in a low humidity state, into the atmosphere, it is possible to ensure that the humidity of the air layer changes according to the humidity of the atmosphere with an appropriate time lag, and it is therefore possible to prevent the color of the cobalt chloride Co of the humidity determining faces M1 to M4 from changing in a relatively short time, that is, it is possible to set the time taken for each of the humidity determining faces M1 to M4 to change color (time required to change color) appropriately without excess or deficiency, and this is effective in preventing the occurrence of an erroneous assessment and problems due to, for example, the time being relatively short. Moreover, the length of the time lag (i.e. the time required to change color) can easily be adjusted by appropriately setting the dispersion density, the inner diameter, etc. of the small holes H according to the intended application, the work environment, etc.

If, for example, the humidity determining faces M1 to M4 faced the small holes H directly (that is, without the front side air layer Au), there would be the problem that there would only be a partial change of color, that is, only of the cobalt chloride Co of the portion of the humidity determining faces M1 to M4 corresponding to the small holes H, and not only would the appearance be impaired, but also it would become difficult to carry out an assessment, but by providing as in this embodiment the front side air layer Au between the small holes H and the humidity determining faces M1 to M4, not only the portion of the humidity determining faces M1 to M4 corresponding to the small holes but also the entire area thereof can undergo a color change uniformly, thus solving the above-mentioned problem.

Furthermore, in particular, the first and second resin films F1 and F2 are formed so as to jut out from the outer peripheral edge of the humidity determining plate P, and the outer peripheral edge portions of the resin films F1 and F2 are bonded directly to each other by the thermal bonding m. Because of this, the outer peripheral edge portion of the base paper B can be covered completely by the first and second resin films F1 and F2, and it is therefore possible to reliably prevent dust from being generated from the cut face on the outer periphery of the base paper B; moreover, since direct bonding of the resin films F1 and F2 can be carried out relatively easily and reliably, the process can be simplified.

Furthermore, the flat back side air layer Ad is formed between the second resin film F2 and the back face of the humidity determining plate P, with at least the region of the back face corresponding to the humidity determining faces M1 to M4 facing the air layer Ad, and the plurality of small holes H', which provide direct communication between the back side air layer Ad and the atmosphere, are formed in the second resin film F2 while being spaced from each other. Because of this, when the humidity indicator I is taken out of the packaging bag DP, etc., moisture in the atmosphere is also transmitted from the back side of the base paper B to the front side air layer Au via the back side air layer Ad and the interior of the base paper B, and it is therefore possible to enhance the sensitivity of the humidity determining faces M1 to M4 on the front side to changes in humidity.

Embodiment 2

Figure 7:
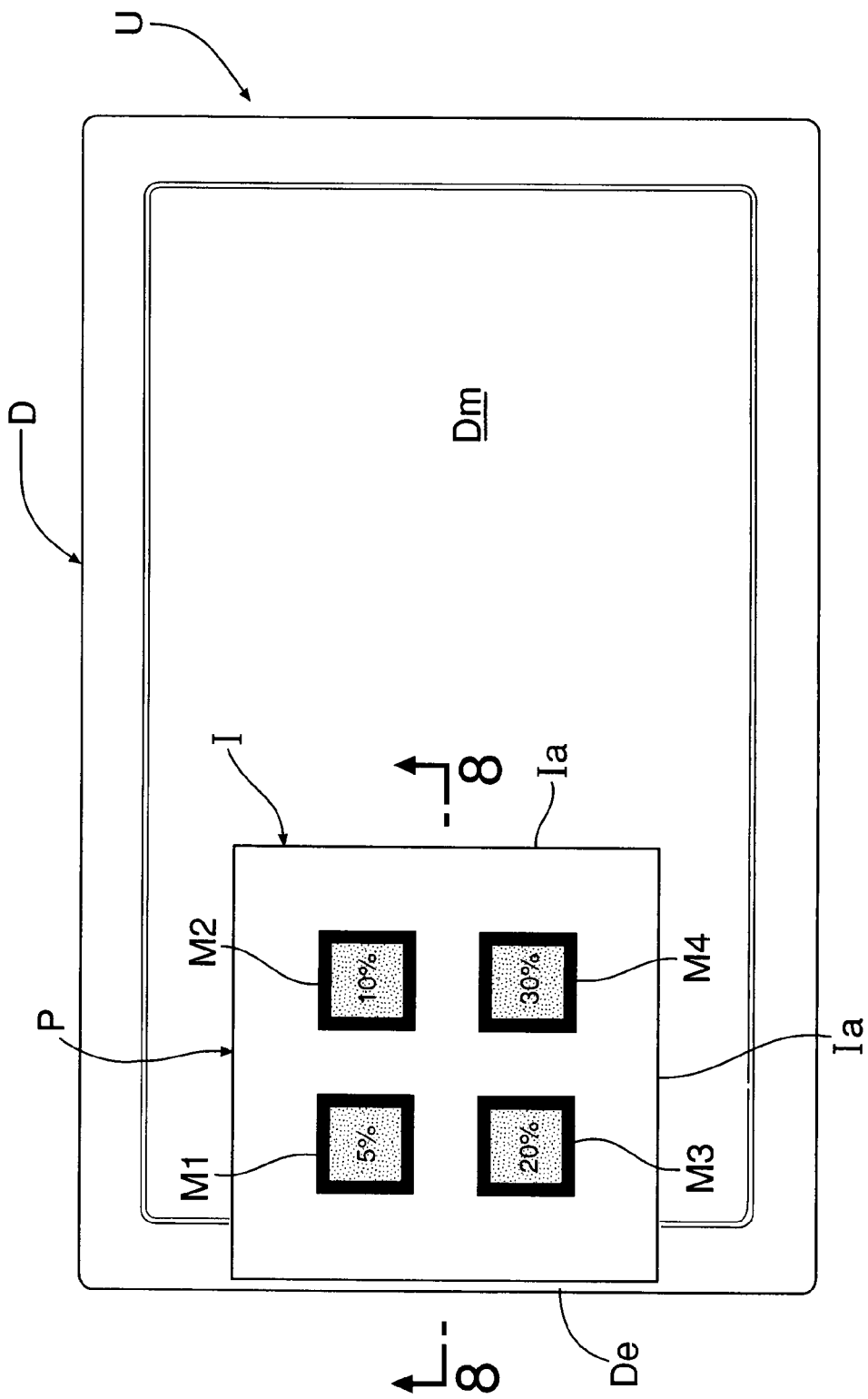
FIG. 7 is a plan view showing a combined unit of a humidity indicator and a desiccant pack related to a second embodiment of the present invention (view corresponding to FIG. 5) (Embodiment 2).
Figure 8:
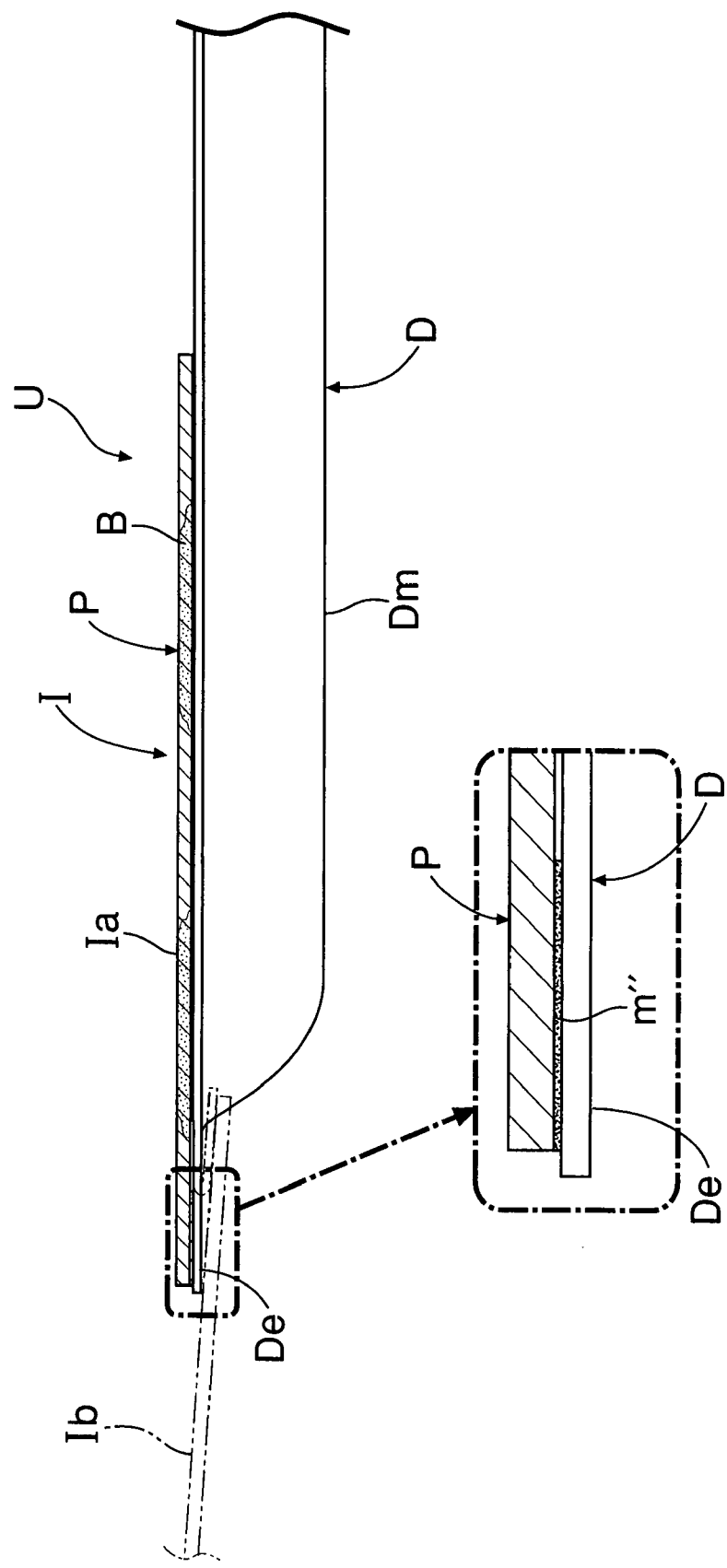
FIG. 8 is an enlarged sectional view along line 8-8 in FIG. 7 and an enlarged partial view thereof (view corresponding to FIG. 6) (Embodiment 2).

A second embodiment of the present invention is now explained by reference to FIG. 7 and FIG. 8. In this embodiment, only the structure of a humidity indicator I is different from that of the first embodiment. That is, in this embodiment, unlike the first embodiment the humidity indicator I is formed only from a flat plate-form humidity determining plate P, and is not covered by the cover body C (that is, the first and second resin films F1 and F2), and the entirety thereof is exposed to the outside. The arrangement of the humidity determining plate P is basically the same as that of the first embodiment, and the cost of the humidity indicator I can be reduced by an amount corresponding to the omission of the cover body C.

One face (in the illustrated example, a back face) of one side end portion of the humidity determining plate P separate from the humidity determining faces M1 to M4 is bonded to one face of one side end portion De, which is flexible, of a desiccant pack D by thermal bonding m", and the humidity indicator I can pivot between a standby position Ia in which the entirety thereof overlaps one face of the desiccant pack D and an in-use position Ib in which a majority thereof overhangs outside from one end edge of the desiccant pack D, with the pivot center in the thermal bonding portion m" or the vicinity thereof. The thermal bonding m" is carried out by, for example, coating at least one of the mutually opposing faces of the one side end portion of the humidity determining plate P and the one side end portion De of the desiccant pack D with a hot-melt material in advance, and heating and pressing into contact the mutually opposing faces by means of a heat pressing machine such as a heat roll.

In this embodiment, basically the same effects as those of the first embodiment can be achieved, apart from the covering effect of the resin films F1 and F2.

Embodiment 3

Figure 9:
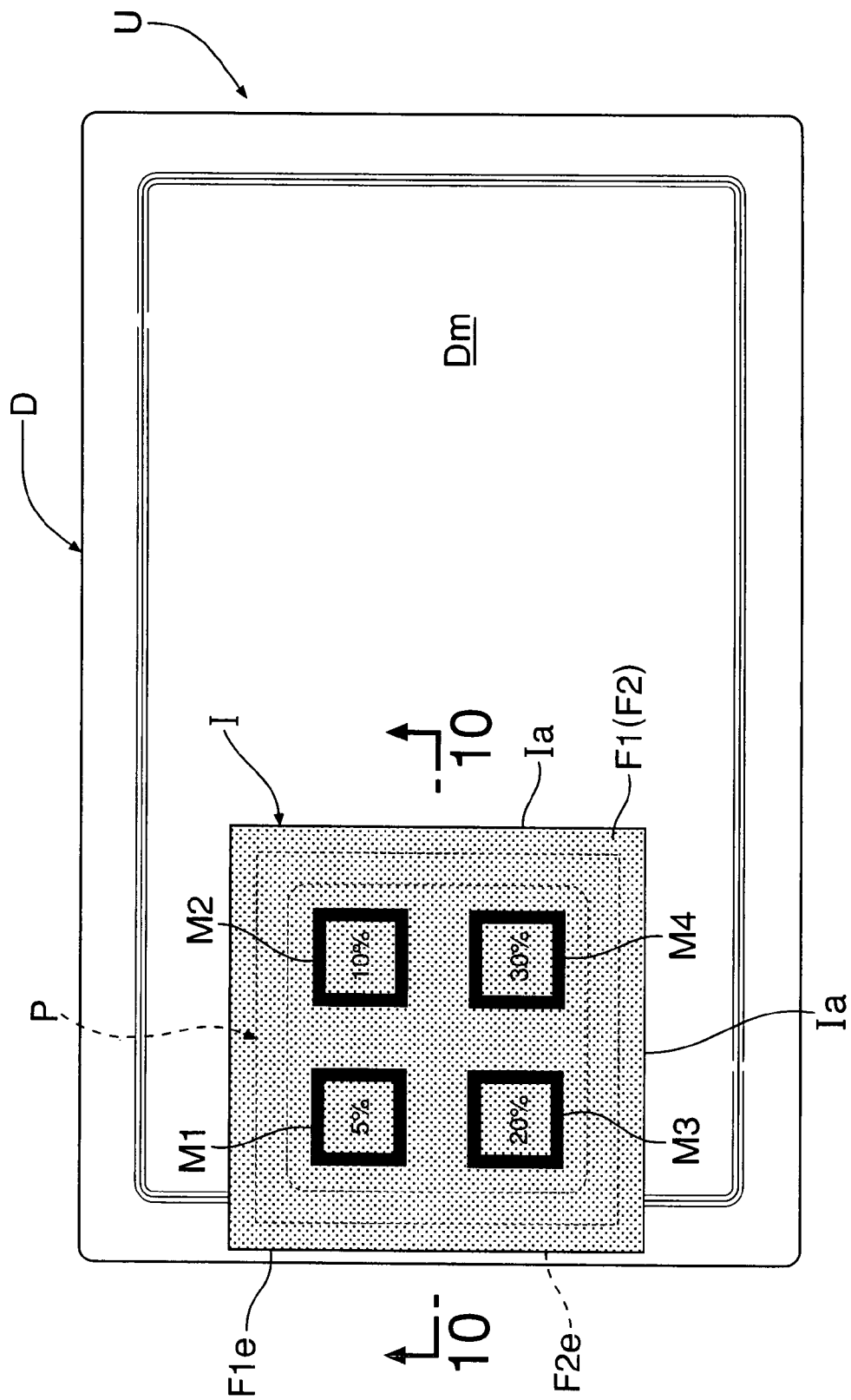
FIG. 9 is plan view showing a combined unit of a humidity indicator and a desiccant pack related to a third embodiment of the present invention (view corresponding to FIG. 5) (Embodiment 3).
Figure 10:
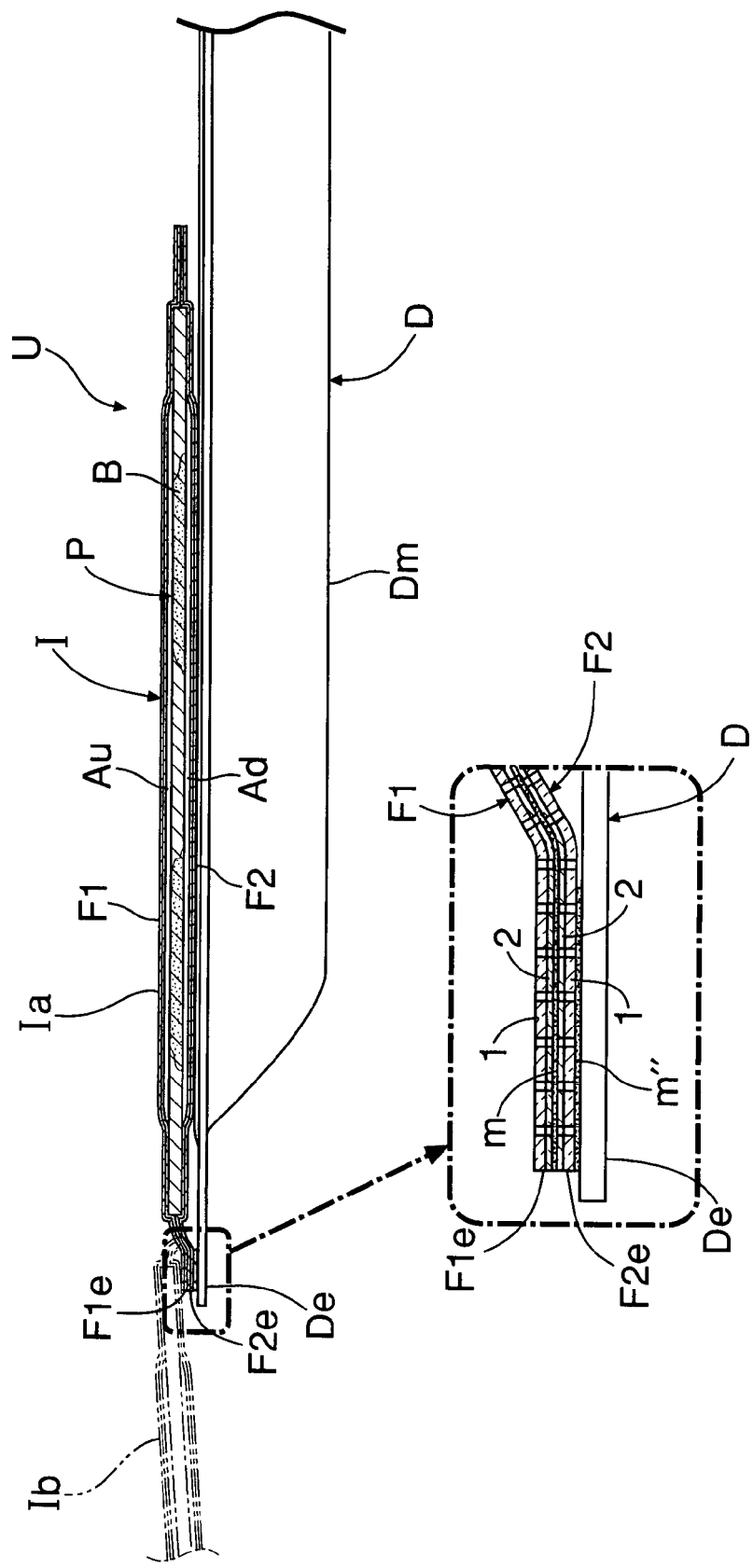
FIG. 10 is an enlarged sectional view along line 10-10 in FIG. 9 and an enlarged partial view thereof (view corresponding to FIG. 6) (Embodiment 3).

A third embodiment of the present invention is now explained by reference to FIG. 9 and FIG. 10. In this embodiment, only the structure of a humidity indicator I (in particular, the structure of a cover body C) is different from that of the first embodiment. That is, in this embodiment, first and second resin films F1 and F2 forming the cover body C of the humidity indicator I are formed so as to have identical dimensions and identical shapes, and unlike the first embodiment there is therefore no extended portion 10 in one end edge portion F1e of the first resin film F1.

One face (in the illustrated example, a back face of the second resin film F2) of one side end portion of the humidity indicator I separate from the humidity determining faces M1 to M4 is bonded to one face of one side end portion De, which is flexible, of a desiccant pack D by thermal bonding m", and the humidity indicator I can pivot between a standby position Ia in which the entirety thereof overlaps one face of the desiccant pack D and an in-use position Ib in which a majority thereof overhangs outside from one end edge of the desiccant pack D, with the pivot center in the thermal bonding portion m" or the vicinity thereof. The thermal bonding m" is carried out by, for example, coating at least one of the mutually opposing faces of the outer face of one side end portion F2e of the second resin film F2 and the one side end portion De of the desiccant pack D with a hot-melt material in advance, and heating and pressing into contact the mutually opposing faces by means of a heat pressing machine such as a heat roll.

In this embodiment, basically the same effects as those of the first embodiment can be achieved, apart from the effect of the extended portion 10.

Embodiments of the present invention are explained in detail above, but the present invention may be modified in a variety of ways as long as the modifications do not depart from the spirit and scope of the present invention.

For example, in the embodiments, four rectangular humidity determining faces M1 to M4 are arranged on the front face of the base paper B lengthwise and widthwise as the humidity determining sections, the humidity determining faces M1 to M4 changing color when the atmospheric humidity increases beyond four humidity limit levels (5%, 10%, 20%, and 30%), but in the present invention there may be any humidity limit, number, arrangement, shape, etc. of the humidity determining faces and they are not limited to those of the embodiments.

Furthermore, in the embodiments, the front side air layer Au is formed as a flat shape so as to encompass all of the plurality of humidity determining faces M1 to M4 as a common air layer that all of the humidity determining faces M1 to M4 face, but in the present invention a front side air layer Au may be formed for an individual humidity determining face or for some humidity determining faces. This also applies to the back side air layer Ad.

Moreover, in the embodiments, the air layers Au and Ad are formed on the front side and back side respectively of the humidity determining plate P, but the back side air layer Ad as the second air layer can be omitted.

Furthermore, in the embodiments, when the humidity indicator I is in the standby position Ia, the humidity determining faces M1 to M4 as the humidity determining sections face the outside, but in the present invention the humidity determining faces M1 to M4 may face the inside, that is, the desiccant pack D side, and in this case since the humidity determining faces M1 to M4 can be positioned closer to the desiccant pack D, assessment of whether or not the indicator I is a defective product can be carried out more reliably.

Moreover, in the embodiments, cobalt chloride is illustrated as a moisture-sensitive material for forming the humidity determining faces M1 to M4 as the humidity determining sections, but in the present invention another moisture-sensitive material that changes color by absorption of moisture may be used to form the humidity determining faces M1 to M4. In this case, the other moisture-sensitive material may be a moisture-sensitive material that is not harmful to the human body.

Furthermore, in the embodiments, thermal bonding means is employed as bonding means, but in the present invention (the first to fourth aspects of the present invention), bonding means in which a bonding portion is not heated may be employed.

The invention claimed is:

1. A combined unit of a humidity indicator and a desiccant pack, the combined unit (U) comprising:
   a humidity indicator (I) having at least one humidity determining section (M1 to M4) provided on a front face of a card-shaped humidity determining plate (P) made of paper and enabling humidity determination to be carried out by a change in color of the humidity determining section (M1 to M4) accompanying the absorption of moisture; and
   a desiccant pack (D) placed together with a moisture-disliking article (E) within a packaging bag (DP) for housing the article (E),
   wherein the humidity indicator (I) has one outer peripheral end bonded to one outer peripheral end of the desiccant pack (D), and wherein the indicator (I) pivots between a standby position (Ia) in which the indicator (I) overlaps one face of the desiccant pack (D) and an in-use position (Ib) in which the indicator (I) overhangs outside from one end edge (De) of the desiccant pack (D), with a pivot center located in the bonding portion or the vicinity thereof.

2. A combined unit of a humidity indicator and a desiccant pack, the combined unit (U) comprising:
   a humidity indicator (I) having at least one humidity determining section (M1 to M4) provided on a front face of a card-shaped humidity determining plate (P) made of paper and enabling humidity determination to be carried out by a change in color of the humidity determining section (M1 to M4) accompanying the absorption of moisture; and
   a desiccant pack (D) placed together with a moisture-disliking article (E) within a packaging bag (DP) for housing the article (E),
   wherein the humidity indicator (I) has one outer peripheral end bonded to one outer peripheral end of the desiccant pack (D), and wherein the indicator (I) pivots between a standby position (Ia) in which at least the humidity determining section (M1 to M4) of the indicator (I) overlaps one face of the desiccant pack (D) and an in-use position (Ib) in which at least the humidity determining section (M1 to M4) of the indicator (I) overhangs outside from one end edge (De) of the desiccant pack (D), with a pivot center located in the bonding portion or the vicinity thereof.

3. The combined unit of a humidity indicator and a desiccant pack according to claim 1 or 2, wherein the front face of the humidity determining plate (P) made of paper is exposed to the outside, and an outer face of one outer peripheral end of the humidity determining plate (P) separate from the humidity determining section (M1 to M4) is bonded to an outer face of the one outer peripheral end of the desiccant pack (D).

4. The combined unit of a humidity indicator and a desiccant pack according to claim 1, wherein the humidity indicator (I) has a transparent first resin film (F1) covering the front face of the humidity determining plate (P) made of paper and a second resin film (F2) covering a back face of the determining plate (P), and outer peripheral edge portions of the two films (F1, F2) are bonded to each other along their entire peripheries at a position jutting out from the one outer peripheral end of the humidity determining plate (P),
   a flat air layer (Au) is formed between the first resin film (F1) and the front face of the humidity determining plate (P), the entire area of the humidity determining section (M1 to M4) facing the air layer (Au), a plurality of small holes (H) providing direct communication between the air layer (Au) and the atmosphere are formed in the first resin film (F1) while being spaced from each other, and
   an outer face of one end portion of either one of the resin films (F1, F2) is bonded to an outer face of the one outer peripheral end of the desiccant pack (D).

5. A combined unit of a humidity indicator and a desiccant pack, the combined unit (U) comprising:
   a humidity indicator (I) having at least one humidity determining section (M1 to M4) provided on a front face of a card-shaped humidity determining plate (P) made of paper and enabling humidity determination to be carried out by a change in color of the humidity determining section (M1 to M4) accompanying the absorption of moisture; and
   a desiccant pack (D) placed together with a moisture-disliking article (E) within a packaging bag (DP) for housing the article (E),
   wherein the humidity indicator (I) has a transparent first resin film (F1) covering the front face of the humidity determining plate (P) and a second resin film (F2) covering a back face of the determining plate (P), and outer peripheral edge portions of the two films (F1, F2) are bonded to each other by thermal bonding (m) along their entire peripheries at a position jutting out from an outer peripheral edge of the humidity determining plate (P),
   a flat air layer (Au) is formed between the first resin film (F1) and the front face of the humidity determining plate (P), the entire area of the humidity determining section (M1 to M4) facing the air layer (Au), and a plurality of small holes (H) providing direct communication between the air layer (Au) and the atmosphere are formed in the first resin film (F1) while being spaced from each other,
   one end edge portion (F1e) of one of the resin films (F1) extends further outside than corresponding one end edge portion (F2e) of the other resin film (F2), an extended portion (10) thereof is bonded by thermal bonding to one outer peripheral end of the desiccant pack (D), and the humidity indicator (I) pivots between a standby position (Ia) in which the indicator (I) overlaps one face of the desiccant pack (D) and an in-use position (Ib) in which the indicator (I) overhangs outside from one outer peripheral end (De) of the desiccant pack (D), with the pivot center located in the thermal bonding portion or the vicinity thereof.

6. The combined unit of a humidity indicator and a desiccant pack according to any one of claim 1, 2, 4, and 5, wherein the humidity determining section (M1 to M4) faces the outside when the humidity indicator (I) is in the standby position (Ia).

7. The combined unit of a humidity indicator and a desiccant pack according to claim 4 or 5, wherein at least said one of the resin films (F1) has a double layer structure of an outer resin layer (1) and an inner resin layer (2) integrally joined to an inner face of the outer resin layer (1), and the inner resin layer (2) is a bonding layer having a lower melting point than that of the outer resin layer (1).

* * * * *